United States Patent
Akabane et al.

(10) Patent No.: US 11,020,327 B2
(45) Date of Patent: Jun. 1, 2021

(54) GEL PASTE COMPOSITION AND COSMETIC USING THE GEL PASTE COMPOSITION

(71) Applicant: SHIN-ETSU CHEMICAL CO., LTD., Tokyo (JP)

(72) Inventors: Emi Akabane, Annaka (JP); Chihiro Hayakawa, Yokohama (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 307 days.

(21) Appl. No.: 15/019,694

(22) Filed: Feb. 9, 2016

(65) Prior Publication Data
US 2016/0262991 A1 Sep. 15, 2016

(30) Foreign Application Priority Data
Mar. 13, 2015 (JP) .............................. JP2015-050670

(51) Int. Cl.
| | | |
|---|---|---|
| *A61K 8/04* | (2006.01) | |
| *A61Q 19/00* | (2006.01) | |
| *A61K 8/37* | (2006.01) | |
| *A61K 8/06* | (2006.01) | |
| *A61Q 1/02* | (2006.01) | |
| *A61Q 1/06* | (2006.01) | |
| *A61K 8/895* | (2006.01) | |
| *C08L 83/12* | (2006.01) | |
| *A61K 8/891* | (2006.01) | |
| *C08G 77/46* | (2006.01) | |
| *C08G 77/12* | (2006.01) | |

(52) U.S. Cl.
CPC .............. *A61K 8/042* (2013.01); *A61K 8/062* (2013.01); *A61K 8/37* (2013.01); *A61K 8/891* (2013.01); *A61K 8/895* (2013.01); *A61Q 1/02* (2013.01); *A61Q 1/06* (2013.01); *A61Q 19/00* (2013.01); *C08L 83/12* (2013.01); *A61K 2800/10* (2013.01); *A61K 2800/43* (2013.01); *A61K 2800/591* (2013.01); *A61K 2800/61* (2013.01); *C08G 77/12* (2013.01); *C08G 77/46* (2013.01)

(58) Field of Classification Search
CPC combination set(s) only.
See application file for complete search history.

(56) References Cited

U.S. PATENT DOCUMENTS

| 4,431,789 A | 2/1984 | Okazaki et al. |
|---|---|---|
| 4,698,178 A | 10/1987 | Huttinger et al. |
| 4,780,145 A | 10/1988 | Mori et al. |
| 4,894,224 A | 1/1990 | Kuwata et al. |
| 5,013,715 A | 5/1991 | Mori et al. |
| 5,118,764 A | 6/1992 | Ichinohe et al. |
| 5,236,986 A | 8/1993 | Sakuta |
| 2002/0028184 A1 | 3/2002 | Sunkel et al. |
| 2002/0058053 A1 | 5/2002 | Nakanishi et al. |
| 2003/0199660 A1 | 10/2003 | Sakuta |
| 2004/0146472 A1 | 7/2004 | Nakanishi |
| 2004/0234477 A1 | 11/2004 | Sakuta |
| 2004/0253197 A1 | 12/2004 | Sakuta |
| 2006/0034875 A1 | 2/2006 | Nakanishi et al. |
| 2006/0110414 A1 | 5/2006 | Suda et al. |
| 2007/0071980 A1 | 3/2007 | Kamei et al. |
| 2011/0015337 A1 | 1/2011 | Sakuta et al. |
| 2011/0117146 A1 | 5/2011 | Inokuchi et al. |
| 2011/0268677 A1 | 11/2011 | Kennan et al. |
| 2012/0251598 A1 | 10/2012 | Ikeda et al. |
| 2015/0037272 A1 | 2/2015 | Ando |
| 2015/0050498 A1 | 2/2015 | Inokuchi |

FOREIGN PATENT DOCUMENTS

| CN | 1533267 A | 9/2004 |
|---|---|---|
| CN | 101208073 A | 6/2008 |
| CN | 101909583 A | 12/2010 |
| CN | 102058492 A | 5/2011 |
| CN | 102271655 A | 12/2011 |
| CN | 102719101 A | 10/2012 |
| CN | 102846599 A | 1/2013 |
| CN | 104220491 A | 12/2014 |
| CN | 104379674 A | 2/2015 |
| EP | 1 424 365 A1 | 6/2004 |
| EP | 2 014 701 A2 | 1/2009 |
| EP | 2 837 649 A1 | 2/2015 |
| EP | 2 898 924 A1 | 7/2015 |
| JP | S61-90732 A | 5/1986 |
| JP | S62-45656 A | 2/1987 |
| JP | S62-54759 A | 3/1987 |
| JP | S62-121764 A | 6/1987 |
| JP | S62-143970 A | 6/1987 |
| JP | S62-143971 A | 6/1987 |
| JP | S62-34039 B2 | 7/1987 |

(Continued)

OTHER PUBLICATIONS

Aug. 31, 2015 Extended European Search Report issued in European Patent Application No. 16000394.3.

(Continued)

*Primary Examiner* — Shobha Kantamneni
(74) *Attorney, Agent, or Firm* — Oliff PLC

(57) ABSTRACT

A gel paste composition including (A) a crosslinking organopolysiloxane and (B) a liquid oil, the crosslinking organopolysiloxane (A) being obtained by reacting an organohydrogenpolysiloxane shown by the following general formula (I) with a polyoxyalkylene compound shown by the following general formula (II) in the presence of a catalyst for hydrosilylation reaction, the component (A) containing polyoxyethylene units in an amount of 20 wt % or more. As a result, the gel paste composition that contains a crosslinking organopolysiloxane having improved compatibility with ethylhexyl methoxycinnamate and water, and thus exhibits excellent dispersibility when blended to a cosmetic thereby providing good feeling and cosmetic sustainability.

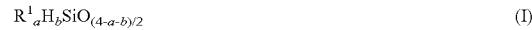

(I)

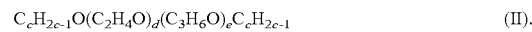

(II).

10 Claims, No Drawings

(56) References Cited

FOREIGN PATENT DOCUMENTS

| | | | |
|---|---|---|---|
| JP | S62-235366 | A | 10/1987 |
| JP | S62-240335 | A | 10/1987 |
| JP | S63-72779 | A | 4/1988 |
| JP | S63-159489 | A | 7/1988 |
| JP | S63-235366 | A | 9/1988 |
| JP | S63-260955 | A | 10/1988 |
| JP | H02-43263 | A | 2/1990 |
| JP | H04-272932 | A | 9/1992 |
| JP | H05-140320 | A | 6/1993 |
| JP | H07-91389 | B2 | 10/1995 |
| JP | H07-330907 | A | 12/1995 |
| JP | H09-59386 | A | 3/1997 |
| JP | 2613124 | B2 | 5/1997 |
| JP | 2844453 | B2 | 1/1999 |
| JP | 2001-055307 | A | 2/2001 |
| JP | 2001-139449 | A | 5/2001 |
| JP | 2002-179798 | A | 6/2002 |
| JP | 2007-119741 | A | 5/2007 |
| JP | 2008-115358 | A | 5/2008 |
| WO | 01/92375 | A1 | 12/2001 |
| WO | 03/024413 | A1 | 3/2003 |
| WO | 2003/020828 | A1 | 3/2003 |
| WO | 2004/024798 | A1 | 3/2004 |
| WO | 2010/080755 | A2 | 7/2010 |

OTHER PUBLICATIONS

Oct. 31, 2019 Office Action issued in Chinese Patent Application No. 201610140439.3.
Nov. 14, 2017 Notification of Reasons for Refusal issued in Japanese Patent Application No. 2015-050670.

GEL PASTE COMPOSITION AND COSMETIC USING THE GEL PASTE COMPOSITION

TECHNICAL FIELD

The present invention relates to a gel paste composition mainly used for a cosmetic, particularly to a gel paste composition that contains a crosslinking organopolysiloxane having affinity with water and ethylhexyl methoxycinnamate (OMC) thereby providing both good applicability and usability, and to a cosmetic using the gel paste composition.

BACKGROUND ART

Silicone oil has conventionally been used as a base oil in many compositions in various fields such as cosmetic. Particularly in skin care and make-up cosmetics, a silicone oil having a low kinematic viscosity of 100 mm$^2$/S or less is widely used due to its properties such as excellent spreadability, light feeling, and reliable safety.

However, when, for example, a pasty composition with low fluidity is prepared from a low viscous silicone oil used as a base oil, it is necessary to use organic materials such as dextrin fatty acid ester (PATENT LITERATURES 1 to 4), sucrose fatty acid ester (PATENT LITERATURE 5), trimethyl-silylated polyvinyl alcohol and trimethyl-silylated polysaccharide (PATENT LITERATURE 6) and fatty acid ester group-containing cellulose ether (PATENT LITERATURE 7), or organic modified clay minerals (PATENT LITERATURES 8 to 10) as a thickener, and the low viscous silicone oil is separated or discharged over time. Thus, conventional techniques fail to achieve a smooth and uniform composition.

To solve this problem, there has been proposed a method for obtaining a uniform pasty composition by using specific organopolysiloxane as a thickener and treating it with a low viscous silicone oil by shear force (PATENT LITERATURE 11). In addition, there has been disclosed a composition obtained by introducing a long-chain alkyl group to a molecule of a crosslinking organopolysiloxane used as a thickener to provide high affinity with hydrocarbon oil and ester oil (PATENT LITERATURE 12).

Meanwhile, skin care and make-up cosmetics mostly include an emulsified composition blended with required components of not only oil but also water. The emulsified compositions are classified into oil-in-water, water-in-oil, and multilayer emulsified compositions according to the type of blending. A composition using the above crosslinking organopolysiloxane as a thickener is certainly excellent in the effect of stably dispersing oil such as a silicone oil, a hydrocarbon oil, and an ester oil, but fails to provide an emulsified composition in which water is also dispersed.

To solve this technical problem, a composition in which a polyoxyalkylene group is introduced in a molecule of crosslinking organopolysiloxane has been proposed to obtain a stable water-in-oil emulsified composition (PATENT LITERATURES 13 and 14). Moreover, a composition that can solve the problem of odor caused over time (PATENT LITERATURE 15) and a composition in which polyglycerin group is introduced as a hydrophilic group (PATENT LITERATURE 16) have been proposed. Further, a crosslinking organopolysiloxane capable of providing a favorable emulsified composition, even using both a silicone oil and an organic oil such as a hydrocarbon oil and an ester oil as the oil has been developed (PATENT LITERATURE 17).

However, the conventional crosslinking organopolysiloxane has low compatibility with an ultraviolet absorber, typified by ethylhexyl methoxycinnamate, and thus fails to ensure storage stability of oil-absorbing and thickened cosmetics. In addition, it is still required to further develop the compatibility with water and the feeling in application.

CITATION LIST

Patent Literature

PATENT LITERATURE 1: Japanese Patent Laid-Open Publication No. S62-121764

PATENT LITERATURE 2: Japanese Patent Laid-Open Publication No. S62-143970

PATENT LITERATURE 3: Japanese Patent Laid-Open Publication No. S62-143971

PATENT LITERATURE 4: Japanese Patent Laid-Open Publication No. S63-159489

PATENT LITERATURE 5: Japanese Patent Laid-Open Publication No. S63-235366

PATENT LITERATURE 6: Japanese Patent Laid-Open Publication No. S62-240335

PATENT LITERATURE 7: Japanese Patent Laid-Open Publication No. S63-260955

PATENT LITERATURE 8: Japanese Patent Laid-Open Publication No. S62-45656

PATENT LITERATURE 9: Japanese Patent Laid-Open Publication No. S62-54759

PATENT LITERATURE 10: Japanese Patent Laid-Open Publication No. S63-72779

PATENT LITERATURE 11: Japanese Patent Laid-Open Publication No. H02-43263

PATENT LITERATURE 12: International Publication No. WO2003/024413

PATENT LITERATURE 13: Japanese Patent Laid-Open Publication No. H04-272932

PATENT LITERATURE 14: Japanese Patent Laid-Open Publication No. H05-140320

PATENT LITERATURE 15: International Publication No. WO2003/20828

PATENT LITERATURE 16: International Publication No. WO2004/24798

PATENT LITERATURE 17: Japanese Patent Laid-Open Publication No. 2008-115358

SUMMARY OF INVENTION

Technical Problem

The present invention was accomplished in view of the above-described problems, and has an object to provide a gel paste composition that contains a crosslinking organopolysiloxane having improved compatibility with ethylhexyl methoxycinnamate and water, and exhibits excellent dispersibility when blended to a cosmetic thereby providing good feeling and cosmetic sustainability.

Solution to Problem

To achieve the above object, the present invention provides a gel paste composition comprising
(A) a crosslinking organopolysiloxane; and
(B) a liquid oil,
the crosslinking organopolysiloxane (A) being obtained by reacting an organohydrogenpolysiloxane shown by the following general formula (I) with a polyoxyalkylene compound shown by the following general formula (II) in the presence of a catalyst for hydrosilylation reaction, the component (A) containing polyoxyethylene units in an amount of 20 wt % or more, $$R^1_a H_b SiO_{(4-a-b)/2} \quad (I)$$

wherein each $R^1$ may be the same or different and represents a substituted or unsubstituted monovalent hydrocarbon group having 1 to 30 carbon atoms and not having an alkenyl group; and "a" and "b" each represent a positive number satisfying $1.0 \leq a \leq 2.5$, $0.001 \leq b \leq 1.2$, and $1.0 \leq a+b \leq 2.6$;

$$C_c H_{2c-1} O(C_2H_4O)_d (C_3H_6O)_e C_c H_{2c-1} \quad (II)$$

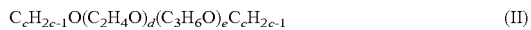

wherein "c" represents an integer of 2 to 6; and "d" and "e" each represent an integer satisfying $5 \leq d \leq 200$ and $0 \leq e \leq 200$.

Such a composition contains a crosslinking organopolysiloxane having improved compatibility with ethylhexyl methoxycinnamate and water. Therefore, when this composition is blended to a cosmetic, the composition exhibits excellent dispersibility and provides good feeling and cosmetic sustainability.

The crosslinking organopolysiloxane (A) is preferably obtained by reacting the organohydrogenpolysiloxane shown by the general formula (I) with the polyoxyalkylene compound shown by the general formula (II) and a polyoxyalkylene compound shown by the following general formula (III) in the presence of the catalyst for hydrosilylation reaction, $$C_c H_{2c-1} O(C_2H_4O)_d (C_3H_6O)_e\text{---}R^2 \quad (III)$$

wherein $R^2$ represents a hydrogen atom, a monovalent hydrocarbon group having 1 to 10 carbon atoms, or —(CO)$R^3$ where $R^3$ represents an alkyl group having 1 to 5 carbon atoms; and "c", "d", and "e" have the same meanings as defined above.

The polyoxyalkylene compound shown by the general formula (III) does not form crosslinking, and thus enables the proportion of polyoxyethylene units to increase without increasing crosslinking density. Accordingly, the component (A) obtained by reacting the compounds shown by the general formulae (I) to (III) has more excellent hydrophilicity, and when the composition containing this component (A) is blended to a cosmetic, the composition exhibits more excellent dispersibility and provides better feeling and cosmetic sustainability.

Alternatively, the crosslinking organopolysiloxane (A) is preferably obtained by reacting the organohydrogenpolysiloxane shown by the general formula (I) with the polyoxyalkylene compound shown by the general formula (II) and an organopolysiloxane shown by the following general formula (IV) in the presence of the catalyst for hydrosilylation reaction, $$R^1_i R^4_j SiO_{(4-i-j)/2} \quad (IV)$$

wherein $R^1$ has the same meaning as defined above; $R^4$ represents an alkenyl group having 2 to 10 carbon atoms; "i" and "j" each represent a positive number satisfying $1.0 \leq i \leq 2.999$, $0.001 \leq j \leq 1.5$, and $1.001 \leq i+j \leq 3$.

The component (A) obtained by reacting the compounds shown by the general formulae (I), (II), and (IV) is more compatible with oil. Accordingly, in the composition containing this component (A), separation between the component (A) and oil hardly occurs.

The organohydrogenpolysiloxane used to obtain the crosslinking organopolysiloxane (A) is preferably shown by the following general formula (V),

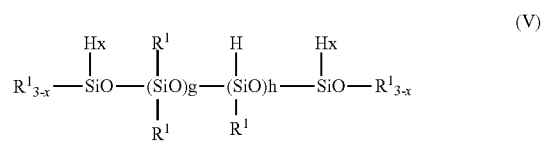

wherein $R^1$ has the same meaning as defined above; "g" and "h" represent an integer satisfying $0 \leq g \leq 300$ and $0 \leq h \leq 300$; "x" is 0 to 2; and $h+x \geq 2$.

When the organohydrogenpolysiloxane shown by the general formula (V) is used as a raw material of the component (A), polymerization reaction progresses smoothly thereby enabling easy preparation of the composition.

The liquid oil (B) is preferably selected from a silicone oil and an ester oil.

Such a component (B) is easily handled when forming a paste, so that the composition containing the component (B) can be easily prepared.

In addition, the present invention provides a cosmetic comprising the inventive gel paste composition.

The cosmetic containing the inventive gel paste composition exhibits good feeling and cosmetic sustainability.

The cosmetic preferably further comprises an oil component (C) other than the liquid oil (B).

Such a cosmetic exhibits better feeling and cosmetic sustainability.

The cosmetic is preferably an emulsified cosmetic and contains water and a water-soluble polymer in a continuous phase.

The oil-in-water (o/w) cosmetic containing water and a water-soluble polymer in the continuous phase is easily produced due to the water-soluble polymer.

The water-soluble polymer is preferably an alkali-thickened vinyl polymer or an acrylamidosulfonic acid polymer.

As to the water-soluble polymer contained in the continuous phase, an alkali-thickened vinyl polymer or an acrylamidosulfonic acid polymer is particularly suitable.

The emulsified cosmetic preferably contains a surface-hydrophobized powder in an oil phase.

Such a cosmetic is further improved in adhesion to the skin and cosmetic sustainability.

The surface-hydrophobized powder is preferably a hydrophobized pigment.

As to the surface-hydrophobized powder, a hydrophobized pigment is particularly suitable.

Advantageous Effects of Invention

The inventive gel paste composition contains a crosslinking organopolysiloxane having improved compatibility with ethylhexyl methoxycinnamate and water. Therefore, when this composition is blended to a cosmetic, the composition exhibits excellent dispersibility and provides good feeling and cosmetic sustainability. The cosmetic containing the inventive gel paste composition thus exhibits good feeling and cosmetic sustainability.

DESCRIPTION OF EMBODIMENTS

Hereinafter, the present invention will be described in detail.

As mentioned above, there has been demanded a gel paste composition that contains a crosslinking organopolysiloxane having improved compatibility with ethylhexyl methoxycinnamate and water, and exhibits excellent dispersibility when blended to a cosmetic thereby providing good feeling and cosmetic sustainability.

The present inventors have earnestly investigated to accomplish the above object. As a result, they found the above problems can be solved by a gel paste composition containing the following components (A) and (B) in which the component (A) contains polyoxyethylene units in an amount of 20 wt % or more, thereby bringing the present invention to completion.

Hereinafter, embodiments of the present invention will be described specifically, but the present invention is not limited thereto.

The present invention is directed to a gel paste composition containing (A) a crosslinking organopolysiloxane and (B) a liquid oil, the crosslinking organopolysiloxane (A) being obtained by reacting an organohydrogenpolysiloxane shown by the following general formula (I) with a polyoxyalkylene compound shown by the following general formula (II) in the presence of a catalyst for hydrosilylation reaction, the component (A) containing polyoxyethylene units in an amount of 20 wt % or more, $$R^1{}_aH_bSiO_{(4-a-b)/2} \quad (I)$$

wherein each $R^1$ may be the same or different and represents a substituted or unsubstituted monovalent hydrocarbon group having 1 to 30 carbon atoms and not having an alkenyl group; and "a" and "b" each represent a positive number satisfying $1.0 \leq a \leq 2.5$, $0.001 \leq b \leq 1.2$, and $1.0 \leq a+b \leq 2.6$;

$$C_cH_{2c-1}O(C_2H_4O)_d(C_3H_6O)_eC_cH_{2c-1} \quad (II)$$

wherein "c" represents an integer of 2 to 6; and "d" and "e" each represent an integer satisfying $5 \leq d \leq 200$ and $0 \leq e \leq 200$.

Such a composition contains a crosslinking organopolysiloxane having improved compatibility with ethylhexyl methoxycinnamate and water. Therefore, when this composition is blended to a cosmetic, the composition exhibits excellent dispersibility and provides good feeling and cosmetic sustainability.

Each component of the inventive gel paste composition is described below.

The crosslinking organopolysiloxane (A) in the present invention is obtained by reacting, as essential components, an organohydrogenpolysiloxane shown by the following general formula (I) with a polyoxyalkylene compound shown by the following general formula (II) in the presence of a catalyst for hydrosilylation reaction, $$R^1{}_aH_bSiO_{(4-a-b)/2} \quad (I)$$

wherein $R^1$, "a", and "b" have the same meanings as defined above, $$C_cH_{2c-1}O(C_2H_4O)_d(C_3H_6O)_eC_cH_{2c-1} \quad (II)$$

wherein "c", "d", and "e" have the same meanings as defined above.

Examples of $R^1$ in the general formula (I) include alkyl groups such as a methyl group, an ethyl group, a propyl group, a butyl group, a pentyl group, a hexyl group, a heptyl group, an octyl group, a nonyl group, and a decyl group; saturated alicyclic hydrocarbon groups such as a cyclopentyl group and a cyclohexyl group; aryl groups such as a phenyl group and a tolyl group; and fluorine-substituted alkyl groups such as a trifluoropropyl group, a nonafluorohexyl group, and a heptadecyl fluorodecyl group. "a" represents 1.0 to 2.5, preferably 1.2 to 2.3. When "a" is less than 1.0, the crosslinking degree is too high to contain water and an ultraviolet absorber such as ethylhexyl methoxycinnamate in sufficient amount, specifically, in an amount equal to or more than the component (A). When "a" is more than 2.5, the crosslinking degree is too low to form a three-dimensional crosslinking structure. "b" is 0.001 to 1.2, preferably 0.005 to 1.0. When "b" is less than 0.001, the crosslinking degree is so low that a three-dimensional crosslinking structure is hardly formed. When "b" is more than 1.2, the crosslinking degree is too high to contain water and an ultraviolet absorber such as ethylhexyl methoxycinnamate in sufficient amount. Moreover, a+b is 1.0 to 2.6, preferably 1.3 to 2.3.

The organohydrogenpolysiloxane may be linear, branched, or cyclic structure; and a linear structure, particularly a linear structure as shown by the general formula (V) is preferable to achieve smooth polymerization reaction.

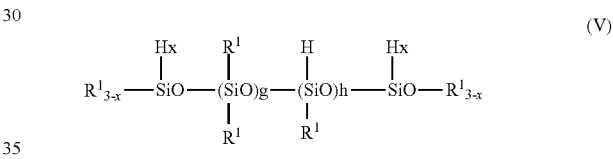

$R^1$ represents a group mentioned above. "g" satisfies $0 \leq g \leq 300$, preferably $0 \leq g \leq 150$, more preferably $0 \leq g \leq 100$. When "g" is 300 or less, the reactivity is not decreased and good usability can be achieved. "h" satisfies $0 \leq h \leq 300$, preferably $1 \leq h \leq 100$, more preferably $2 \leq h \leq 50$. When "h" is 300 or less, the crosslinking degree is not excessively increased to contain water and an ultraviolet absorber such as ethylhexyl methoxycinnamate in sufficient amount. "x" is 0 to 2, preferably 0 to 1. Moreover, the total of "h" and "x" should be 2 or more to form a crosslinking structure.

In the general formula (II), "d" satisfies $5 \leq d \leq 200$, preferably $5 \leq d \leq 100$; "e" satisfies $0 \leq e \leq 200$, preferably $5 \leq e \leq 100$. To make the obtained composition absorb water, $d/e \geq 1$ is preferable.

Any combination is possible between the organohydrogenpolysiloxane shown by the general formula (I) and the polyoxyalkylene compound shown by the general formula (II) so long as the component (A) contains polyoxyethylene units in an amount of 20 wt % or more. The polyoxyethylene unit content is preferably 25 wt % or more, more preferably 30 wt % or more. The polyoxyethylene unit content of less than 20 wt % with respect to the component (A) leads to lack of hydrophilicity. On the other hand, the polyoxyethylene unit content is preferably 60 wt % or less, more preferably 50 wt % or less, with respect to the component (A). The polyoxyethylene unit content of 60 wt % or less with respect to the component (A) allows sufficient compatibility with an ultraviolet absorber such as ethylhexyl methoxycinnamate.

The organohydrogenpolysiloxane may be further reacted with a polyoxyalkylene compound shown by the following general formula (III) to obtain the component (A). This polyoxyalkylene compound dose not form crosslinking, and thus enables the proportion of polyoxyethylene units to increase without increasing crosslinking density.

$$C_cH_{2C-1}O(C_2H_4O)_d(C_3H_6O)_e-R^2 \quad (III)$$

wherein $R^2$ represents a hydrogen atom, a monovalent hydrocarbon group having 1 to 10 carbon atoms, or —(CO)$R^3$ where $R^3$ represents an alkyl group having 1 to 5 carbon atoms; and "c", "d", and "e" have the same meanings as defined above.

Examples of $R^2$ include, besides a hydrogen atom, saturated aliphatic hydrocarbon groups such as a methyl group, an ethyl group, a propyl group, a butyl group, a pentyl group, a hexyl group, a heptyl group, an octyl group, a nonyl group, and a decyl group. Examples of $R^3$ include saturated aliphatic hydrocarbon groups such as a methyl group, an ethyl group, a propyl group, a butyl group, and a pentyl group. "c", "d", and "e" are as described above.

The polyoxyalkylene compound shown by the general formula (III) may be added during the reaction of the organohydrogenpolysiloxane shown by the general formula (I) and the polyoxyalkylene compound shown by the general formula (II). Alternatively, the component (A) may be synthesized by 2-step reaction in which the organohydrogenpolysiloxane shown by the general formula (I) is reacted with the polyoxyalkylene compound shown by the general formula (II) (or the general formula (III)) and then the polyoxyalkylene compound shown by the general formula (III) (or the general formula (II)) is added thereto. To control the addition reaction and keep stable quality, the 2-step reaction is preferable.

The organohydrogenpolysiloxane may be further reacted with an organopolysiloxane shown by the following general formula (IV) to obtain the component (A).

$$R^1_iR^4_jSiO_{(4-i-j)/2} \quad (IV)$$

wherein $R^1$ has the same meaning as defined above; $R^4$ represents an alkenyl group having 2 to 10 carbon atoms; "i" and "j" each represent a positive number satisfying $1.0 \leq i \leq 2.999$, $0.001 \leq j \leq 1.5$, and $1.001 \leq i+j \leq 3$.

$R^4$ represents an alkenyl group having 2 to 10 carbon atoms, for example, a monovalent hydrocarbon group having 2 to 10 carbon atoms and vinyl group at the terminal. Illustrative examples thereof include alkenyl groups such as a vinyl group and an allyl group; a vinyl group is preferable. "i" satisfies $1.0 \leq i \leq 2.999$. When "i" is 1.0 or more, good compatibility with oil can be achieved. When "i" is 2.999 or less, sufficient hydrophilicity can be achieved. "j" satisfies $0.001 \leq j \leq 1.5$. When "j" is 0.001 or more, good compatibility with oil can be achieved. When "j" is 1.5 or less, the reaction rate is not remarkably decreased due to steric hindrance. Moreover, i+j is 1.001 to 3, preferably 1.2 to 2.5. The organopolysiloxane shown by the general formula (IV) may be linear, branched, or cyclic structure; and a linear structure is particularly preferable to achieve smooth polymerization reaction. The organopolysiloxane may contain two or more $R^4$ in the molecule, which serves as a crosslinker in the component (A), or may contain one $R^4$ in the molecule, which serves as a side chain in the component (A). Among them, organopolysiloxane containing one $R^4$ in the molecule is preferable since the reaction is easily controlled. In this case, the reaction conditions are in accordance with PATENT LITERATURE 17.

To obtain the crosslinking organopolysiloxane of component (A), the raw materials of the component (A) (e.g., the organohydrogenpolysiloxane shown by the general formula (I), the polyoxyalkylene compound shown by the general formula (II)) may be reacted in the presence of a catalyst for hydrosilylation reaction such as a platinum compound (e.g. chloroplatinic acid, alcohol-modified chloroplatinic acid, a chloroplatinic acid-vinylsiloxane complex) or a rhodium compound. The reaction temperature is preferably, but is not particularly limited to, 20 to 120° C. In the hydrosilylation reaction, the mole ratio of the total aliphatic unsaturated group/SiH is not particularly limited, but preferably in the range of 1/10 to 10/1, more preferably 8/10 to 3/1.

The hydrosilylation reaction may be performed without solvent or in the presence of a later-described liquid oil (B). If necessary, an organic solvent may be used. Examples of the organic solvent include aliphatic alcohols such as methanol, ethanol, 2-propanol, and butanol; aromatic hydrocarbons such as benzene, toluene, and xylene; aliphatic or alicyclic hydrocarbons such as n-pentane, n-hexane, and cyclohexane; halogenated hydrocarbons such as dichloromethane, chloroform, and carbon tetrachloride; and ketone solvents such as acetone and methylethyl ketone. In view of cosmetic use, the reaction is preferably performed without solvent, or with ethanol or 2-propanol.

To prevent a by-product formed by intramolecular rearrangement of an alkenyl group during the hydrosilylation from decomposing over time and generating ketone and aldehydes, which cause odor, the crosslinking organopolysiloxane of component (A) may be purified with an acidic substance, as needed. The purification treatment can be performed only with water without adding an acidic substance, but it is preferable to add an acidic substance selected from organic acid, inorganic acid, and salts thereof in order to keep the reaction constant. The amount of the acidic substance to be added is 0.01 to 10 parts by mass, preferably 0.02 to 5 parts by mass, based on 100 parts by mass of the organopolysiloxane. When the amount is 0.01 part by mass or more, excellent deodorant effect is expected. When it is 10 parts by mass or less, a neutralized salt is not precipitated in the composition after the treatment. The organic acid may be added directly, or preferably added as an aqueous solution of 1 to 50 mass %. The purification treatment is preferably performed by adding 5 to 50 parts by mass of an aqueous solution of the acidic substance to 100 parts by mass of the crosslinking polymer, in view of contact efficiency. The aqueous solution of the acidic substance is generally adjusted to have a pH of 2 to 5. The pH is preferably 3 to 5 since the lower pH may cause unfavorable reaction such as cutting of a siloxane chain.

After adding the acidic substance, heating is preferably performed at 20 to 150° C., in particular 50 to 100° C., although not necessarily needed. In addition, a basic neutralizer may be added after adding the acidic substance. In this case, the basic neutralizer may be added directly, or preferably added as an aqueous solution of 1 to 50 mass %. The amount of the basic neutralizer to be added is such an amount that functional group equivalent ratio of the acidic substance to the basic neutralizer is in the range of 1/0.1 to 0.1/1, preferably 1/0.3 to 0.3/1, and the pH after neutralization is adjusted to 5 to 8. The treatment condition after adding the basic neutralizer is 20 to 150° C., preferably 20 to 80° C.

Illustrative examples of the acidic substance include citric acid, lactic acid, tartaric acid, malic acid, glutamic acid, acetic acid, glycine, potassium dihydrogenphosphate, and succinic acid. In particular, citric acid, lactic acid, and glutamic acid are preferable. Illustrative examples of the basic neutralizer include sodium carbonate, sodium hydrogen carbonate, sodium hydroxide, potassium hydroxide, disodium hydrogenphosphate, and sodium acetate. In particular, sodium carbonate, sodium hydrogen carbonate, and sodium hydroxide are preferable.

The acidic substance and the basic neutralizer are preferably selected from combinations that produce a neutralized salt having a pH buffer effect. In this manner, not only odor is reduced but also the pH of the composition can be stabilized. The treatment method is in accordance with the method disclosed in PATENT LITERATURES 15 and 16.

The method of calculating the content of oxyethylene unit (polyoxyethylene unit) in the crosslinking organopolysiloxane (A) will now be described. When the organohydrogenpolysiloxane is shown by the following general formula:

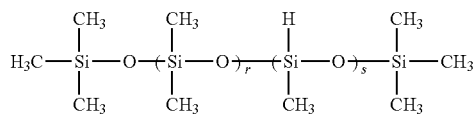

the molecular weight is calculated by the following formula:

Molecular weight=162+74×$r$+60×$s$      [i]

When the polyoxyalkylene compound is shown by the following general formula:

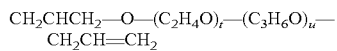

the molecular weight and the content of oxyethylene unit are obtained by the following formulae:

Molecular weight=98+44×$t$+58×$u$      [ii]

Content of oxyethylene unit=44×$t$      [iii]

Assuming that the charged mole ratio of the polyoxyethylene compound to the organohydrogenpolysiloxane is w, the content of oxyethylene unit (mass %) in the crosslinking organopolysiloxane can be obtained by the following formula:

Content of oxyethylene unit=[$iii$]×w/([$ii$]×w+[$i$])×100

(B) Liquid Oil

The liquid oil used in the present invention preferably has a kinematic viscosity at 25° C. of 0.65 to 10,000 mm$^2$/s because of good handleability when forming a paste. Examples of the liquid oil include silicone oil, natural vegetable and animal fatty oil, semi-synthetic oil, higher fatty acid, higher alcohol, hydrocarbon oil, and ester oil. When an apparatus capable of heating a sample uniformly, such as disperser, is used, the kinematic viscosity at 25° C. of the oil may exceed the above upper limit.

Illustrative examples of the silicone oil include linear or branched organopolysiloxane such as dimethyl polysiloxane, tristrimethylsiloxymethylsilane, caprylyl-methicone, phenyl trimethicone, diphenylsiloxyphenyl trimethicone, tetrakis trimethylsiloxysilane, methylphenyl polysiloxane, methylhexyl polysiloxane, methylhydrogen polysiloxane, and dimethylsiloxane/methylphenylsiloxane copolymer; cyclic organopolysiloxanes such as octamethyl cyclotetrasiloxane, decamethyl cyclopentasiloxane, dodecamethyl cyclohexasiloxane, tetramethyl tetrahydrogen cyclotetrasiloxane, and tetramethyltetraphenyl cyclotetra siloxane; silicone rubbers such as amino-modified organopolysiloxane, pyrrolidone-modified organopolysiloxane, pyrrolidone carboxylate-modified organopolysiloxane, gum dimethyl polysiloxane with high polymerization degree, gum amino-modified organopolysiloxane, and gum dimethylsiloxane/methylphenylsiloxane copolymer; a cyclic organopolysiloxane solution of silicone gum or rubber, trimethylsiloxysilicate, a cyclicsiloxane solution of trimethylsiloxysilicate, higher alkoxy-modified silicone such as stearoxysilicone, higher fatty acid-modified silicone, alkyl-modified silicone, long chain alkyl-modified silicone, amino acid-modified silicone, fluorine-modified silicone. Illustrative examples of the fluorinated oil include perfluoro polyether, perfluoro decalin, and perfluoro octane.

Illustrative examples of the natural vegetable and animal fatty oil and the semi-synthetic oil include avocado oil, almond oil, olive oil, lever oil, apricot kernel oil, wheat germ oil, sesame oil, rice germ oil, rice bran oil, sasanqua oil, safflower oil, squalane, squalene, soybean oil, tea seed oil, camellia oil, evening primrose oil, corn oil, rapeseed oil, persic oil, castor oil, methyl ester of castor oil fatty acid, sunflower oil, grape seed oil, jojoba oil, a macadamia nut oil, mink oil, meadow foam oil, cotton seed oil, peanut oil, liquid lanolin, and egg-yolk oil.

Illustrative examples of the higher fatty acid include undecylenic acid, oleic acid, linoleic acid, linolenic acid, arachidonic acid, eicosapentaenoic acid, docosahexaenoic acid, isostearic acid, and lactic acid. Illustrative examples of the higher alcohol include oleyl alcohol, isostearyl alcohol, hexyl decanol, octyl dodecanol, cetostearyl alcohol, 2-decyl tetradecynol, and monooleyl glyceryl ether (selachyl alcohol).

The hydrocarbon oil may be exemplified by a linear or cyclic hydrocarbon oil. However, oil that is a solid at room temperature such as ceresin and vaseline is not suitable for the liquid oil (B) in view of usability. Illustrative examples thereof include an α-olefin oligomer, light isoparaffin, light liquid isoparaffin, squalane, synthetic squalane, vegetable squalane, squalene, liquid paraffin, and liquid isoparaffin.

Illustrative examples of the ester oil include diisobutyl adipate, 2-hexyldecyl adipate, di-2-heptylundecyl adipate, diisopropyl sebacate, di-2-ethylhexyl sebacate, diisostearyl malate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl oleate, decyl oleate, neopentyl glycol dioctanoate, neopentyl glycol dicaprate, triethyl citrate, 2-ethylhexyl succinate, amyl acetate, butyl acetate, isocetyl stearate, butyl stearate, cetyl lactate, octyldodecyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, hexyl laurate, and 2-octyldodecyl N-lauroyl-L-glutamate ester.

Among the ester oil, illustrative examples of glyceride oil include triethylhexanoin, glyceryl triisooctanoate, glyceryl triisostearate, caprylic/capric triglyceride, glyceryl monostearate, glyceryl di-2-heptylundecanoate, glyceryl trimyristate, and diglyceryl myristate isostearate.

The mixing ratio (A)/(B) of the crosslinking organopolysiloxane (A) to the liquid oil (B) of the inventive gel paste composition is preferably 1/20 to 20/1 (mass ratio), particularly preferably 1/10 to 1/1.

In the production of the inventive gel paste composition, the crosslinking organopolysiloxane (A) and the liquid oil (B) may be mixed with a conventional stirrer, or preferably kneaded by shear force. The reason why kneading is preferable is that the crosslinking organopolysiloxane (A) has a three-dimensional crosslinking structure which does not dissolve in a solvent and a paste composition with smooth appearance can be obtained by giving dispersibility by shear force. Kneading may be performed with, for example, a 3-roll mill, a 2-roll mill, a kneader, a mass-colloider, a sand grinder, a colloid mill, a Gaulin homogenizer, a disperser, or a high shear mixer. In particular, a 3-roll mill or a disperser is preferably used.

In addition, the present invention provides a cosmetic containing the inventive gel paste composition. The inventive cosmetic preferably contains, as component (C), an oil component other than the liquid oil (B). The oil component may be any of a solid, semi-solid, or liquid oil which is conventionally used for cosmetics. The oil component may be a mixture of two or more oils. Preferable is a liquid oil component; illustrative examples thereof are same as the liquid oil (B).

The inventive cosmetic may contain any other components, as needed. Examples of the components include components conventionally used for cosmetics, such as an ultraviolet absorber, an ultraviolet absorbing-scattering agent, a compound having alcoholic hydroxyl group, a water-soluble or water-swelling polymer, a powder, a surfactant, an oily thickener, an oily film-forming agent, a preservative, an antioxidant, a pH adjusting agent, a chelating agent, an algefacient, an anti-inflammatory agent, and other agents, but it is not particularly limited.

Examples of the ultraviolet absorber include ethylhexyl methoxycinnamate, polysilicone-15, octocrylene, tert-butyl methoxydibenzoylmethane, methylene bis-benzotriazolyl tetramethylbutylphenol, octyl salicylate, homosalate, phenylbenzimidazole sulfonic acid, hydroxy methoxybenzophenone sulfonic acid, 2-ethylhexyl para-dimethylaminoazobenzoate, hexyl dimethylaminohydroxybenzoylbenzoate, bis-ethylhexyl oxyphenol methoxyphenyl triazine.

Examples of the ultraviolet absorbing-scattering agent include particulate titanium oxide, particulate titanium oxide containing iron, particulate zinc oxide, particulate cerium oxide, and a composite material thereof. A dispersed material obtained by dispersing a powder of the ultraviolet absorbing-scattering agent into oil previously may also be used.

The compound having alcoholic hydroxyl group is used for moisturizing and refreshing or used as a preservative or solvent; examples thereof include lower alcohols such as ethanol and isopropyl alcohol; sugar alcohols such as sorbitol and maltose; polyhydric alcohols such as butyleneglycol, propyleneglycol, dipropyleneglycol, pentyleneglycol, glycerin, ethylhexyl glycerin. The blending amount is preferably in the range of 0.1 to 30 mass % of the whole cosmetic.

The water-soluble or water-swelling polymer is used for adjusting feeling such as viscosity adjusting, film forming, and moisturizing of a cosmetic. Examples thereof include plant polymers such as an Arabia gum, tragacanth, galactan, a guar gum, a karaya gum, carrageenan, pectin, agar, quince seed (marmelo), starch (rice, corn, potato, wheat, and so on), an algae colloid, and a locust bean gum; microbial polymers such as a xanthan gum, dextran, succinoglucan, and pullulan; animal polymers such as collagen, casein, albumin, and gelatin; starch polymers such as carboxymethyl starch and methyl hydroxypropyl starch; cellulose polymers such as methyl cellulose, ethyl cellulose, methyl hydroxypropyl cellulose, carboxymethyl cellulose, hydroxymethyl cellulose, hydroxypropyl cellulose, nitrocellulose, and sodium carboxymethyl cellulose; polyethylene glycol polymers; alginic acid polymers such as sodium alginate and propylene glycol alginate ester; film-forming agents such as polyvinyl alcohol and polyvinyl pyrrolidone; vinyl polymers such as a carboxyvinyl polymer and an (acrylates/C10-30 alkyl acrylate) crosspolymer, acrylic polymers such as sodium polyacrylate, an (ammonium acryloyldimethyl taurate/VP) copolymer, sodium acryloyldimethyl taurate copolymer, (sodium acrylate/sodium acryloyldimethyl taurate) copolymer, (hydroxyethyl acrylate/sodium acryloyldimethyl taurate) copolymer, and polyacrylamide; and other synthetic water-soluble polymers such as polyethyleneimine and a cationic polymer. The blending amount of the water-soluble or water-swelling polymer is preferably in the range of 0.1 to 25 mass % of the whole cosmetic.

When an o/w cosmetic is produced by using the inventive gel paste composition, a water-soluble polymer selected from an alkali-thickened vinyl polymer such as a carboxyvinyl polymer and an (acrylates/C10-30 alkyl acrylate) crosspolymer and an acrylamidosulfonic acid (AMPS) polymer composed of AMPS monomer is preferably blended. In this case, the continuous phase contains water and a water-soluble polymer. The AMPS polymer is a thickener having a high yield value and excellent resistance to shear. Accordingly, the AMPS polymer facilitates the production of the inventive cosmetic.

As to the powder, any powder may be used regardless of its shape (spherical, acicular, plate-like, etc.), particle size (fumed, microparticle, pigment-class, etc.), and particle structure (porous, non-porous, etc.). Examples thereof include an inorganic powder, an organic powder, a metal soap, and a colorant (e.g., inorganic pigments such as metal powder pigment, a tar dye, a natural dye, and a pearl pigment). The powder component may be surface-treated with a metal soap, silica, aluminum oxide, aluminum hydroxide or other by a known method or may be a composite powder to suppress the surface activity, enhance the dispersibility, and improve feeling when the cosmetic is applied.

Examples of the inorganic powder include titanium oxide, zinc oxide, barium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, a metal tungstate salt, hydroxyapatite, vermiculite, higilite, bentonite, montmorillonite, hectorite, zeolite, ceramics powder, calcium hydrogenphosphate, alumina, aluminum hydroxide, boron nitride, and silica.

Examples of the organic powder include polyester powder, polyethylene powder, polystyrene powder, polyurethane powder, polymethylmethacrylate powder, methyl methacrylate crosspolymer, cellulose powder, silk powder, nylon powder such as Nylon 12 and Nylon 6, fibrous powder thereof, crosslinked silicone fine powder having crosslinking structure from dimethylpolysiloxane, crosslinked polymethylsylsesquioxane spherical fine powder, fine powder obtained by coating the surface of crosslinking organopolysilicone elastomer with polymethylsylsesquioxane particles, laminated powder of a resin, starch powder, fatty acid starch derivatives powder, and lauroyl lysine.

Examples of the metal soap include zinc stearate, aluminum stearate, calcium stearate, magnesium stearate, zinc myristate, and magnesium myristate.

Examples of the colorant include inorganic pigments such as titanium oxide, iron oxide, titanium black, carbon black, chromium hydroxide, chromium oxide, iron blue, ultramarine blue, and aluminum powder; tar dyes such as Red No. 226 and Yellow No. 4; natural dyes such as carmine; pearl pigments such as titanium mica, synthetic phlogopite, titanium mica coated with iron oxide, and synthetic phlogopite coated with titanium oxide.

Moreover, these powders may be compound or treated with general oil, silicone oil, fluorine compound, surfactant, reactive organohydrogenpolysiloxane, organopolysiloxane having a hydrolysable alkoxysilane group, or an acryl-silicone copolymer having hydrolysable silyl group. These powders may be used solely or in combination of two or more kinds.

In particular, the cosmetic of o/w type preferably contains (disperses) a surface-hydrophobized powder in the oil phase to reduce flowing down of the powder after the cosmetic is applied. In this way, adhesion to the skin and cosmetic sustainability are more improved. Illustrative examples of the powder are as described above. Especially, the surface-hydrophobized powder is preferably a hydrophobized pigment.

The blending amount of the powder is preferably in the range of 0.1 to 99 mass % of the whole cosmetic. In particular, in the case of a powder-solid cosmetic, the amount is preferably in the range of 80 to 99 mass % of the whole cosmetic.

The powder may be blended to the inventive cosmetic directly, or a dispersed material obtained by dispersing the powder to a dispersion medium previously may be used. Examples of the usable dispersion medium are the same as the liquid oil. A dispersant may be used in the preparation of the dispersed material. Preferable examples of the dispersant include a dispersant generally used for dispersing powder and acryl silicone KP-578 (available from Shin-Etsu Chemical Co., Ltd.).

The surfactants include an anionic, a cationic, a nonionic and an amphoteric surfactant. In the present invention, there is no particular restriction, and thus any surfactant may be used provided that the surfactant is used in a usual cosmetic.

Above all, nonionic surfactant is often used in cosmetics for skin. Well-known examples thereof include surfactants whose hydrophobic group is a hydrocarbon group such as sorbitan fatty acid esters, glycerin fatty acid esters, polyglycerin fatty acid esters, propylene glycol fatty acid esters, sucrose fatty acid esters, methyl glucoside fatty acid esters, alkyl polyglucoside, polyoxyalkylene fatty acid esters, and polyoxyethylene cured castor oil.

In addition, a silicone surfactant is used for the purpose of emulsion and dispersion of a water-in-oil emulsion and stabilization thereof. Examples thereof include a polyoxyalkylene-modified organopolysiloxane (Japanese Patent No. 2137062, Japanese Patent Laid-Open Publication No. H07-330907), an organopolysiloxane co-modified with polyoxyalkylene and alkyl (Japanese Patent Laid-Open Publication No. S61-90732 and No. H09-59386), a silicone-branched organopolysiloxane modified with polyoxyalkylene and a silicone-branched organopolysiloxane co-modified with polyoxyalkylene and long-chain alkyl (Japanese Patent Laid-Open Publication No. 2001-055307), an organopolysiloxane modified with polyglycerin (Japanese Patent Laid-Open Publication No. S62-34039, Japanese Patent No. 2613124, Japanese Patent No. 2844453, and Japanese Patent Laid-Open Publication No. 2002-179798), an organopolysiloxane co-modified with polyglycerin and long-chain alkyl, a silicone-branched organopolysiloxane modified with polyglycerin and a silicone-branched organopolysiloxane co-modified with polyglycerin and long-chain alkyl (Japanese Patent Laid-Open Publication No. 2002-179798). Further, crosslinking polyorganosiloxane having a hydrophilic group within the molecule such as (dimethicone/(PEG-10/15)) crosspolymer may also be used. Examples of commercial products thereof include KSG-210, 710, 310, 340, 810, 850Z (available from Shin-Etsu Chemical Co., Ltd.).

Examples of the oily thickener include particulate silica such as silylated silica; organic modified clay minerals such as disteardimonium hectorite; metal soaps such as aluminum stearate; polysaccharide fatty acid esters such as dextrin palmitate/2-ethylhexanoate and inulin stearate; sucrose fatty acid esters such as sucrose stearate acetate; and crosslinking organopolysiloxane other than the component (A).

The crosslinking organopolysiloxane other than the component (A) preferably swells with a larger weight of a liquid oil than its own weight, and may contain at least one moiety selected from the group consisting of a polyoxyalkylene moiety, a polyglycerin moiety, an alkyl moiety, an alkenyl moiety, aryl moiety, and a fluoroalkyl moiety in the molecule. Examples of commercial products thereof include KSG series (available from Shin-Etsu Chemical Co., Ltd.), which is made pasty with oil. These crosslinking organopolysiloxane is not sticky but light feeling and excellent in thickening and stabilization of an oily or w/o cosmetic.

Examples of the oily film-forming agent include α-olefin/vinyl pyrrolidone copolymers such as eicosene/vinyl pyrrolidone copolymer, acrylic acid/alkylacrylate copolymer, acryl/silicone graft or block copolymers, and silicone network resins such as trimethylsiloxy silicate. The silicone network resin may contain a pyrolidone moiety, long-chain alkyl moiety, polyoxyalkylene moiety, fluoroalkyl moiety, and anion moiety such as carboxylic acid in the molecule.

Examples of the preservative include para-oxybenzoate alkyl ester, benzoic acid, sodium benzoate, sorbic acid, potassium sorbate, and phenoxy ethanol. Illustrative example of the antibacterial agent includes benzoic acid, salicylic acid, carbolic acid, sorbic acid, a para-oxybenzoate alkyl ester, p-chloro-m-cresol, hexachlorophen, benzalkonium chloride, chlorhexidine chloride, trichlorocarbanilide, a photosensitive element, phenoxy ethanol, and a combination thereof.

Examples of the antioxidant include tocopherol, butyl hydroxyl anisole, dibutyl hydroxyl toluene, phytic acid, and a combination thereof. Examples of the pH adjusting agent include lactic acid, citric acid, glycolic acid, succinic acid, tartaric acid, dl-malic acid, potassium carbonate, sodium bicarbonate, and ammonium bicarbonate. Examples of the chelating agent include alanine, sodium edetate, sodium polyphosphate, sodium metaphosphate, and phosphoric acid. Examples of the algefacient include L-menthol and camphor. Example of the anti-inflammatory agent includes allantoin, glycyrrhizinic acid and its salt, glycyrrhetic acid, stearyl glycyrrhetinate, tranexamic acid, and azulene.

Examples of the other agents to be added as needed include amino acids such as glycine, serine, arginine and glutamic acid, and derivatives thereof; nicotine acid and vitamin such as vitamin A including vitamin A oil and retinol, vitamin B including such as pyridoxine hydrochloride, panthenol, pantothenyl ethyl ether, nicotinic-acid amide and cyanocobalamine, vitamin C including ascorbyl palmitate and ascorbyl glucoside, and vitamin E including α-tocopherol, and derivatives thereof; and anti-inflammatory agent such as dipotassium glycyrrhizate.

Examples of the inventive cosmetic include skin care cosmetics such as milky lotion, cream, cleansing cream, pack, oil liquid, massage material, cosmetic liquid, cleansing lotion, deodorant, hand cream, and lip cream; make-up cosmetics such as make-up foundation, white powder, liquid foundation, oil foundation, rouge, eye shadow, mascara, eye liner, eye brow, and lipstick; hair cosmetics such as shampoo, rinse, treatment, and setting material; antiperspirants; ultraviolet-protective cosmetics such as sunscreen lotion, and sunscreen cream. The cosmetic can be in the form of a liquid, an emulsion, a cream, a solid, a paste, a gel, a powder, a press, a multilayer, a mousse, a spray, a stick, and so on.

EXAMPLES

Hereinafter, the present invention will be specifically described with reference to examples and comparative example, but the present invention is not limited to the following examples.

(A) Synthesis of Crosslinking Organopolysiloxane

Synthesis Example 1

Into a reactor were put 83.2 g of an organohydrogenpolysiloxane shown by the following average composition formula (1) (Set molecular weight: 4,162), 143.9 g of a polyoxyalkylene shown by the following average composition formula (P1) (Set molecular weight: 2,878), 340 g of isopropyl alcohol, and 0.06 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

45.4 g of 1% citric acid aqueous solution was added thereto, and heat treatment was performed at 70 to 80° C. for 3 hours under mixing. 36.3 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

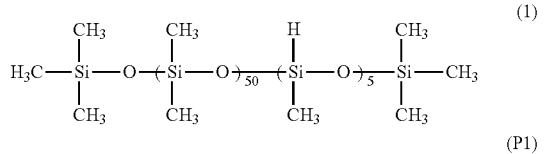
(1)

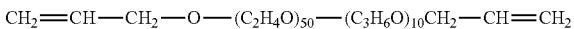
(P1)

Synthesis Example 2

Into a reactor were put 83.2 g of an organohydrogenpolysiloxane shown by the average composition formula (1), 150.9 g of a polyoxyalkylene shown by the following average composition formula (P2) (Set molecular weight: 3,018), 352 g of isopropyl alcohol, and 0.06 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

46.8 g of 1% citric acid aqueous solution was added thereto, and heat treatment was performed at 70 to 80° C. for 3 hours under mixing. 37.4 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

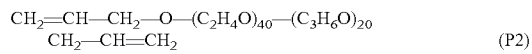
(P2)

Synthesis Example 3

Into a reactor were put 83.2 g of an organohydrogenpolysiloxane shown by the average composition formula (1), 157.9 g of a polyoxyalkylene shown by the following average composition formula (P3) (Set molecular weight: 3,158), 362 g of isopropyl alcohol, and 0.06 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

48.2 g of 1% citric acid aqueous solution was added thereto, and heat treatment was performed at 70 to 80° C. for 3 hours under mixing. 38.4 g of 2% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

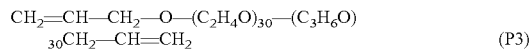
(P3)

Synthesis Example 4

Into a reactor were put 61.0 g of an organohydrogenpolysiloxane shown by the following average composition formula (2) (Set molecular weight: 2,136), 75.8 g of a polyoxyalkylene shown by the following average composition formula (P4) (Set molecular weight: 758), 137 g of isopropyl alcohol, and 0.05 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

27.4 g of 1% citric acid aqueous solution was added thereto, and heat treatment was performed at 70 to 80° C. for 3 hours under mixing. 21.9 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

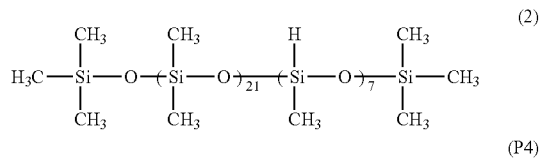
(2)

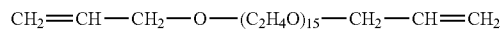
(P4)

Synthesis Example 5

Into a reactor were put 52.6 g of an organohydrogenpolysiloxane shown by the following average composition formula (3) (Set molecular weight: 2,104), 37.9 g of a polyoxyalkylene shown by the average composition formula (P4), 90.5 g of isopropyl alcohol, and 0.03 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

40.8 g of 1% citric acid aqueous solution was added thereto, and heat treatment was performed at 70 to 80° C. for 3 hours under mixing. 32.6 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

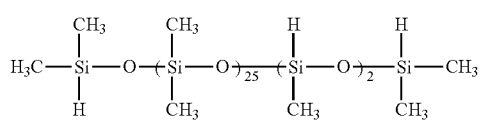
(3)

Synthesis Example 6

Into a reactor were put 93.0 g of an organohydrogenpolysiloxane shown by the following average composition formula (4) (Set molecular weight: 3,718), 150.9 g of a polyoxyalkylene shown by the average composition formula (P2), 163 g of isopropyl alcohol, and 0.05 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

48.8 g of 1% citric acid aqueous solution was added thereto, and heat treatment was performed at 70 to 80° C. for 3 hours under mixing. 39.0 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

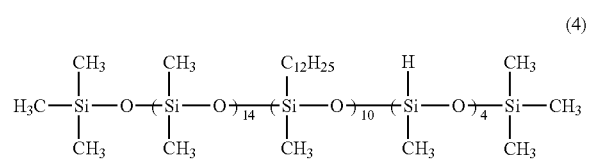
(4)

Synthesis Example 7

Into a reactor were put 83.2 g of an organohydrogenpolysiloxane shown by the following average composition formula (5) (Set molecular weight: 3,274), 25.7 g of, an organopolysiloxane shown by the following average composition formula (6) (Set molecular weight: 1,284), and 0.01 g of an ethanol solution of 3 mass % chloroplatinic acid; and the mixture was stirred at 70 to 80° C. for 1 hour to obtain an organohydrogenpolysiloxane shown by the following average composition formula (7). Then, 120.7 g of a polyoxyalkylene shown by the average composition formula (P2), 216 g of isopropyl alcohol, and 0.05 g of an ethanol solution of 3 mass % chloroplatinic acid were added thereto, and the mixture was stirred at 70 to 80° C. for 3 hours to obtain a polyoxyalkylene-crosslinking organopolysiloxane.

45.9 g of 1% citric acid aqueous solution was added thereto, and heat treatment was performed at 70 to 80° C. for 3 hours under mixing. 36.7 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

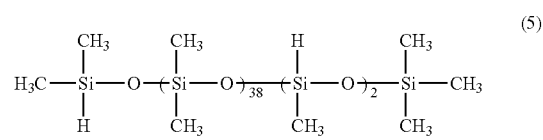
(5)

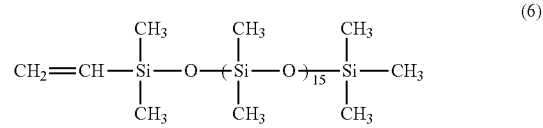
(6)

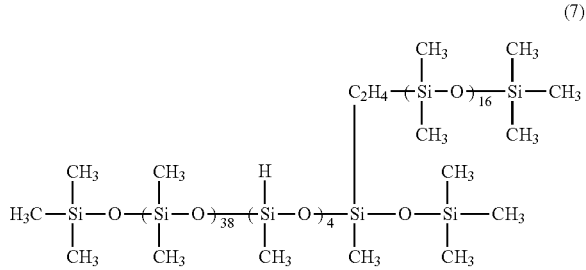
(7)

Synthesis Example 8

Into a reactor were put 66.6 g of an organohydrogenpolysiloxane shown by the average composition formula (1), 33.6 g of a polyoxyalkylene shown by the following average composition formula (P5) (Set molecular weight: 2,098), 0.01 g of an ethanol solution of 3 mass % chloroplatinic acid, and 90 g of isopropyl alcohol; and the mixture was stirred at 70 to 80° C. for 1 hour to obtain a polyoxyalkylene-modified organohydrogenpolysiloxane shown by the following average composition formula (8). Then, 101.6 g of a polyoxyalkylene shown by the average composition formula (P2), 90 g of isopropyl alcohol, and 0.05 g of an ethanol solution of 3 mass % chloroplatinic acid were added thereto, and the mixture was stirred at 70 to 80° C. for 3 hours to obtain a polyoxyalkylene-crosslinking organopolysiloxane.

40.2 g of 1% citric acid aqueous solution was added thereto, and heat treatment was performed at 70 to 80° C. for 3 hours under mixing. 32.1 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

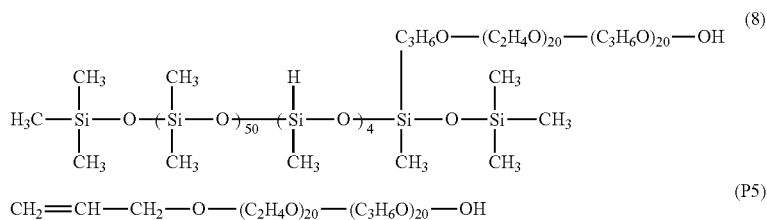

(8)

CH₂=CH—CH₂—O—(C₂H₄O)₂₀—(C₃H₆O)₂₀—OH  (P5)

Comparative Synthesis Example 1

Into a reactor were put 104.4 g of an organohydrogenpolysiloxane shown by the following average composition formula (9) (Set molecular weight: 6,262), 19.0 g of a polyoxyalkylene shown by the average composition formula (P4), 123.3 g of isopropyl alcohol, and 0.02 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

24.7 g of 1% citric acid aqueous solution was added thereto, and heat treatment was performed at 70 to 80° C. for 3 hours under mixing. 19.8 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

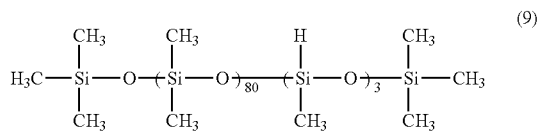

Comparative Synthesis Example 2

Into a reactor were put 145.8 g of an organohydrogenpolysiloxane shown by the following average composition formula (10) (Set molecular weight: 5,832), 79.0 g of a polyoxyalkylene shown by the average composition formula (P3), 225 g of isopropyl alcohol, and 0.04 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

45.0 g of 1% citric acid aqueous solution was added thereto, and heat treatment was performed at 70 to 80° C. for 3 hours under mixing. 35.8 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining the polyoxyalkylene-crosslinking organopolysiloxane treated with acid.

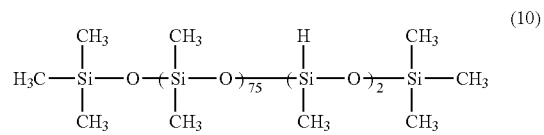

Table 1 shows water absorption property, ethylhexyl methoxycinnamate (OMC) absorption property, and ethyleneoxide unit content (polyoxyethylene unit content) calculated from the setting structure of the crosslinking organopolysiloxane obtained in synthesis examples 1 to 8 and comparative synthesis examples 1 and 2.

To evaluate the absorption property, the crosslinking organopolysiloxane was mixed with the same amount of water or OMC by stirring, and the appearance was then observed. The evaluation criteria are as follows:
Good: Absorption and swelling occurred.
Fair: The mixture was not separated but its surface was wet.
Poor: A part of water (or OMC) was not absorbed.

TABLE 1

|  | Synthesis example | | | | | | | | Comparative synthesis example | |
|---|---|---|---|---|---|---|---|---|---|---|
|  | 1 | 2 | 3 | 4 | 5 | 6 | 7 | 8 | 1 | 2 |
| Ethyleneoxide content (wt %) | 48 | 38 | 27 | 48 | 37 | 36 | 36 | 40 | 3 | 3 |
| Water absorption property | good | good | good | good | good | good | good | good | poor | poor |
| OMC absorption property | good | good | good | good | good | good | good | good | poor to fair | good |

As shown in Table 1, the crosslinking organopolysiloxanes in synthesis examples 1 to 8, which contain polyoxyethylene units in amount of 20 wt % or more with respect to the whole siloxane, were excellent in compatibility with water and OMC (water and OMC absorption properties). On the other hand, the crosslinking organopolysiloxanes in comparative synthesis examples 1 and 2, in which the polyoxyethylene unit content with respect to the whole siloxane is not 20 wt % or more, were poor in compatibility with water and OMC (water and OMC absorption properties).

Mixing Component (A) with Liquid Oil (B) into a Paste

The crosslinking organopolysiloxane (A) obtained in synthesis examples was mixed with a liquid oil (B), methylphenyl silicone oil (KF-56A available from Shin-Etsu Chemical Co., Ltd.), to form a paste. Then, emulsion was prepared to check the dispersibility in water.

[Forming Paste]

50 g of the crosslinking organopolysiloxane and 50 g of the KF-56A were mixed and dispersed, and the mixture was kneaded by shear force with a 3-roll. Further KF-56A was added to obtain a gel paste composition having crosslinking organopolysiloxane concentration of 20%.

[Preparing Emulsion and Checking Dispersibility]

10 g of the obtained gel paste composition and 10 g of water were mixed and stirred with a dispersion mixer at 1,000 rpm for 2 minutes. Into a 200-mL beaker was poured 150 g of water and added 0.1 g of the obtained emulsion while stirring gently. After 5 minutes from the completion of adding the emulsion, dispersibility was checked with the naked eye and evaluated as shown in Table 2.

Y-I: The emulsion was fully dispersed in water.
Y-II: The emulsion was partially dispersed in water.
Y-III: The emulsion was not dispersed in water at all.

In addition, as shown in the following example 9, it is possible to previously mix the liquid oil (B) during the synthesis of the crosslinking organopolysiloxane (A) to form a paste.

Example 9

Into a reactor were put 74.4 g of an organohydrogenpolysiloxane shown by the average composition formula (4), 120.7 g of a polyoxyalkylene shown by the average composition formula (P2), 81.3 g of isopropyl alcohol, 48.8 g of isononyl isononanoate, and 0.05 g of an ethanol solution of 3 mass % chloroplatinic acid. The mixture was stirred for 3 hours while keeping the temperature within the reactor at 70 to 80° C. to obtain a polyoxyalkylene-crosslinking organopolysiloxane.

39.0 g of 1% citric acid aqueous solution was added thereto, and heat treatment was performed at 70 to 80° C. for 3 hours under mixing. 31.2 g of 1% sodium hydrogen carbonate aqueous solution was then added, and the solution was stirred at 40 to 50° C. for 1 hour. After completion of stirring, the temperature was increased to 100° C. under reduced pressure to remove volatile components, thereby obtaining a mixture of the polyoxyalkylene-crosslinking organopolysiloxane treated with acid and isononyl isononanoate. The obtained mixture was kneaded with a 3-roll, and isononyl isononanoate was further added to dilute the mixture until the concentration of the polyoxyalkylene-crosslinking organopolysiloxane reached 20% thereby obtaining a pasty composition.

Examples 10 to 12 and Comparative Examples 3 to 5

The inventive gel paste composition was used as inner phase, and a dispersed and emulsified (simply referred to as emulsified below) cosmetic (an o/w cream) was produced with the composition shown in Table 3 (the values are

TABLE 2

| | Example | | | | | | | | Comparative example | |
|---|---|---|---|---|---|---|---|---|---|---|
| | example 1 | example 2 | example 3 | example 4 | example 5 | example 6 | example 7 | example 8 | Comparative example 1 | Comparative example 2 |
| (A) | Synthesis example 1 | Synthesis example 2 | Synthesis example 3 | Synthesis example 4 | Synthesis example 5 | Synthesis example 6 | Synthesis example 7 | Synthesis example 8 | Comparative synthesis example 1 | Comparative synthesis example 2 |
| Dispersibility | Y-I | Y-I | Y-I | Y-I | Y-II | Y-I | Y-II | Y-I | Y-III | Y-III |

As shown in Table 2, examples 1 to 8 demonstrated that the emulsion was dispersed in water. On the other hand, comparative examples 1 and 2, in which the crosslinking organopolysiloxane does not have polyoxyethylene unit content of 20 wt % or more with respect to the whole siloxane, demonstrated that the emulsion was not dispersed in water at all.

expressed by mass %). The emulsion states were then compared. The production procedure of the cream was as follows: components 5 to 7 in Table 3 were mixed uniformly; the mixture was stirred at 2,500 rpm with a dispersion mixer; components 1 to 4 in Table 3 were each added slowly.

TABLE 3

| | Component | Example 10 | Example 11 | Example 12 | Comparative example 3 | Comparative example 4 | Comparative example 5 |
|---|---|---|---|---|---|---|---|
| 1 | gel paste 1 (*1) | 10 | | | | | |
| 2 | gel paste 2 (*2) | | 10 | 10 | | | |
| 3 | gel paste 3 (*3) | | | | 10 | | |
| 4 | KSG-16 | | | | | 10 | 10 |
| 5 | carboxyvinyl polymer gel (*4) | 37.5 | 37.5 | 37.5 | 37.5 | 37.5 | 37.5 |
| 6 | water | 52.5 | 52.5 | 52 | 52.5 | 52.5 | 52 |
| 7 | surfactant (*5) | | | 0.5 | | | 0.5 |

(*1) Gel paste 1: a composition obtained by mixing the crosslinking organopolysiloxane in synthesis example 4 with KF-56A into a paste (crosslinking organopolysiloxane concentration: 25%)
(*2) Gel paste 2: a composition obtained by mixing the crosslinking organopolysiloxane in synthesis example 5 with KF-56A into a paste (crosslinking organopolysiloxane concentration: 25%)
(*3) Gel paste 3: a composition obtained by mixing the crosslinking organopolysiloxane in comparative synthesis example 1 with KF-56A into a paste (crosslinking organopolysiloxane concentration: 25%)
(*4) Carboxyvinyl polymer gel: gel obtained by adding Carbopol 980 (available from Lubrizol Corporation) into water slowly under stirring to disperse it, and neutralizing the dispersion with diisopropanol amine (polymer concentration: 1%)
(*5) Surfactant: Polysorbate 80

The emulsion states of the creams were compared with the naked eye. Consequently, examples 10 to 12 were emulsified homogeneously. In general, an emulsion using an oily component as inner phase requires a surfactant with high HLB (Hydrophilic-Lipophilic Balance) such as component 7, however, examples using the inventive gel paste composition enabled an emulsion without a surfactant. In this case, the appearance was white like the usual cream.

The cream in comparative example 3 was rough and non-homogeneous, and agglomerates were detected therein with the naked eye. The crosslinking organopolysiloxane used in comparative example 3 has a low content of hydrophilic group and thus forms w/o emulsion. Therefore, the w/o gel, the surface of which has low hydrophilicity, was supposed to agglomerate.

The component 4, KSG-16 (available from Shin-Etsu Chemical Co., Ltd.), used in comparative examples 4 and 5 is a gel paste obtaining by swelling a crosslinking organopolysiloxane having no hydrophilic group with dimethyl silicone oil. The appearance in comparative example 4 was translucent, and agglomerates having a size of 1 mm or more were found with the naked eye. Thus, the cream was not emulsified uniformly.

The appearance of the cream in comparative example 5 was relatively white to comparative example 4, but coarse particles were still found and the cream was not homogeneous. These results indicates that the conventional crosslinking organopolysiloxane is not easy to be emulsified even when a surfactant is used.

In general, as described above, a surfactant with high HLB is required to blend an oily component into water (to emulsify uniformly). However, it is known that the surfactant remaining on the skin after the cosmetic is applied causes skin irritation and is easily washed down by sweat or water. Moreover, addition of the surfactant makes deforming under reduced pressure difficult in the production of cosmetics in some cases. On the other hand, as shown in examples 10 to 12, the inventive gel paste composition enables an oily component to be blended into water without a surfactant or with a small amount of a surfactant. Accordingly, the inventive gel paste can reduce the problems caused by a surfactant.

Feeling evaluation was made with respect to the applied cosmetics in example 10 and comparative example 5. 10 expert panels were surveyed about feeling in use and finish. The evaluation was ranked on a scale of 1 to 3: "example 10 is preferred"; "cannot say"; "comparative example 5 is preferred".

Consequently, as to "fitting to the skin", 10 panels answered that example 10 was preferred. As to "stickiness after application", there was no significant difference. As to "finish smoothness", 7 panels answered that example 10 was preferred; the other 3 answered that cannot say.

The elastomer gel used in comparative example 5 is a silicone oil having low viscosity and little stickiness, which is supposed to be the reason of good result regarding stickiness.

Example 13 o/w Sunscreen

Components 1 and 2 shown in Table 4 were mixed uniformly, and the mixture was slowly added to a solution in which components 3 to 9 in Table 4 had been dissolved uniformly, under stirring with a dispersion mixer to obtain an o/w sunscreen. The sunscreen thus obtained exhibited fresh and light feeling and little stickiness.

TABLE 4

| | Component | Example 13 (wt %) |
|---|---|---|
| 1 | gel paste 2 (*2) | 5 |
| 2 | OMC | 5 |
| 3 | carboxyvinyl polymer gel (*4) | 37.5 |
| 4 | glycerin | 3 |
| 5 | dipropylene glycol | 3 |
| 6 | ethanol | 2 |
| 7 | preservative | appropriate |
| 8 | antioxidant | appropriate |
| 9 | purified water | remainder |

(*2) (*4) the same as Table 3

Example 14 o/w Sunscreen

Components 1 to 4 shown in Table 5 were mixed uniformly, and the mixture was slowly added to a solution in which components 5 to 12 in Table 5 had been dissolved uniformly, under stirring with a dispersion mixer to obtain an o/w sunscreen. The sunscreen thus obtained exhibited fresh and light feeling and little stickiness.

TABLE 5

|   | Component | Example 14 (wt %) |
|---|---|---|
| 1 | gel paste 1 (*1) | 10 |
| 2 | OMC | 7.5 |
| 3 | octocrylene | 2.5 |
| 4 | Uvinul A+ (*6) | 1 |
| 5 | dipropylene glycol | 5 |
| 6 | KF-6100 (*7) | 0.4 |
| 7 | KF-6104 (*7) | 0.2 |
| 8 | SIMULGEL600 (*8) | 0.6 |
| 9 | Aristoflex AVC 5% aqueous solution (*9) | 13 |
| 10 | antioxidant | appropriate |
| 11 | preservative | appropriate |
| 12 | water | remainder |

(*1) the same as Table 3
(*6) ultraviolet absorber: diethylamino hydroxybenzoyl hexyl benzoate (available from BASF Co., Ltd.)
(*7) polyglycerin-modified silicone oil (available from Shin-Etsu Chemical Co., Ltd.)
(*8) acrylamide/sodium acryloyldimethyl taurate copolymer (available from SEPPIC Inc.)
(*9) 5% aqueous solution of (ammonium acryloyldimethyl taurate/VP) copolymer (available from Clariant Corporation)

Example 15 o/w Sunscreen

Components 1 to 4 shown in Table 6 were mixed uniformly, and the mixture was slowly added to a solution in which components 5 to 13 in Table 6 had been dissolved uniformly, under stirring with a dispersion mixer to obtain an o/w sunscreen. The sunscreen thus obtained exhibited fresh and light feeling and little stickiness.

TABLE 6

|   | Component | Example 15 (wt %) |
|---|---|---|
| 1 | gel paste 1 (*1) | 3.0 |
| 2 | SPD-T5 (*10) | 12.5 |
| 3 | SPD-Z5 (*11) | 17.5 |
| 4 | KF-6104 (*12) | 0.3 |
| 5 | KF-6100 (*13) | 0.6 |
| 6 | dipropylene glycol | 3.0 |
| 7 | SIMULGEL600 (*8) | 1.2 |
| 8 | PEG-80 hydrogenerated castor oil | 0.13 |
| 9 | Aristoflex AVC 5% aqueous solution (*9) | 13.0 |
| 10 | sodium chloride 1% aqueous solution | 8.0 |
| 11 | antioxidant | appropriate |
| 12 | preservative | appropriate |
| 13 | water | remainder |

(*1) the same as Table 3
(*8) and (*9) the same as Table 5
(*10) particulate titanium oxide dispersed in cyclopentasiloxane (available from Shin-Etsu Chemical Co., Ltd.)
(*11) particulate zinc oxide dispersed in cyclopentasiloxane (available from Shin-Etsu Chemical Co., Ltd.)
(*12) polyglyceryl-3-polydimethylsiloxyethyl dimethicone (available from Shin-Etsu Chemical Co., Ltd.)
(*13) polyglyceryl-3-disiloxane dimethicone (available from Shin-Etsu Chemical Co., Ltd.)

Example 16 o/w Liquid Foundation

Components 2 to 6 shown in Table 7 were dispersed with a 3-roll. Component 1 in Table 7 was added thereto and mixed uniformly to prepare an oil phase. The oil phase was slowly added to a solution in which components 7 to 10 in Table 7 had been dissolved uniformly, under stirring with a dispersion mixer to obtain an o/w emulsion (liquid foundation). The liquid foundation thus obtained exhibited little stickiness and fitted to the skin.

TABLE 7

|   | Component | Example 16 (wt %) |
|---|---|---|
| 1 | gel paste 1 (*1) | 15 |
| 2 | trimethyl hexanoin | 3.5 |
| 3 | hydrophobized titanium oxide (*14) | 8.5 |
| 4 | hydrophobized black titanium oxide (*14) | 1 |
| 5 | hydrophobized bengala (*14) | 0.4 |
| 6 | hydrophobized yellow iron oxide (*14) | 0.1 |
| 7 | carboxyvinyl polymer gel (*4) | 37.5 |
| 8 | antioxidant | appropriate |
| 9 | preservative | appropriate |
| 10 | water | remainder |

(*1) (*4) the same as Table 3
(*14) a powder surface-treated with KF-9909 (triethoxysilylethylpolydimethylsiloxyethylhexyl dimethicone, available from Shin-Etsu Chemical Co., Ltd.)

Example 17

Lipstick

Components 1 to 12 shown in Table 8 were heated and mixed uniformly. To the mixture were added components 13 and 14 in Table 8 and mixed uniformly. A container was filled with the resulting mixture to obtain a lipstick of an oily solid.

Other examples of the stick-type oily solid cosmetic include concealer and foundation. The inventive gel paste composition enables these cosmetics to exhibit little stickiness, smooth spreadability, and light feeling.

TABLE 8

|   | Component | Example 17 (wt %) |
|---|---|---|
| 1 | candelilla wax | 4 |
| 2 | polyethylene | 2 |
| 3 | microcrystalline wax | 3 |
| 4 | gel paste 2 (*2) | 5.5 |
| 5 | OMC | 3 |
| 6 | KF-561P (*15) | 13.5 |
| 7 | KF-54 (*16) | 20 |
| 8 | KP-545 (*17) | 10 |
| 9 | KF-6105 (*18) | 3 |
| 10 | macadamia nut oil | 20 |
| 11 | hydrogenated polyisobutene | 10 |
| 12 | isotridecyl isononanoate | 6 |
| 13 | colorant | appropriate |
| 14 | mica | appropriate |

(*2) the same as Table 3
(*15) stearyl-modified acryl silicone resin (available from Shin-Etsu Chemical Co., Ltd.)
(*16) diphenyl dimethicone (available from Shin-Etsu Chemical Co., Ltd.)
(*17) acryl silicone dissolved in decamethylcyclopenta-siloxane (available from Shin-Etsu Chemical Co., Ltd.)
(*18) alkyl-modified branched polyglycerin-modified silicone (available from Shin-Etsu Chemical Co., Ltd.)

Example 18

Concealer

All components shown in Table 9 were mixed uniformly to obtain an oily concealer. By adding a pigment thereto, a cosmetic foundation can also be obtained. A cosmetic fitting to the skin could be obtained by blending the inventive gel paste composition.

TABLE 9

| | Component | Example 18 (wt %) |
|---|---|---|
| 1 | gel paste 4 (*19) | 5 |
| 2 | KSG-15 (*20) | 55 |
| 3 | KSG-16 | 15 |
| 4 | decamethylcyclopentasiloxane | 15 |
| 5 | KSP-100 (*21) | 8 |
| 6 | KMP-590 (*22) | 2 |

(*19) Gel paste 4: a composition obtained by mixing the crosslinking organopolysiloxane in synthesis example 3 with KF-56A into a paste (crosslinking organopolysiloxane concentration: 25%)
(*20) a gel paste obtained by swelling a crosslinking organopolysiloxane having no hydrophilic group with decamethylcyclopentasiloxane (available from Shin-Etsu Chemical Co., Ltd.)
(*21) a silicone composite powder having an average particle size of 5 μm (available from Shin-Etsu Chemical Co., Ltd.)
(*22) a silicone resin powder having an average particle size of 2 μm (available from Shin-Etsu Chemical Co., Ltd.)

Example 19

Mousse Foundation

Components 1 to 8 shown in Table 10 were mixed with a 3-roll. Components 9 to 14 in Table 10 were added thereto and mixed to obtain a mousse foundation of a non-aqueous type. The obtained cosmetic exhibited good adhesion and light feeling.

TABLE 10

| | Component | Example 19 (wt %) |
|---|---|---|
| 1 | KSG-16 | 25 |
| 2 | gel paste 2 (*2) | 5 |
| 3 | dimethicone (6cs) | 11.2 |
| 4 | neopentylglycol diehexanoate | 5 |
| 5 | dimethyl-silylated silica | 0.5 |
| 6 | iron oxide (*23) | appropriate |
| 7 | titanium oxide (*23) | appropriate |
| 8 | particulate titanium oxide | 8 |
| 9 | KF-7312J (*24) | 10 |
| 10 | decamethylcyclopentasiloxane | 11 |
| 11 | KSP-105 (*25) | 2 |
| 12 | PMMA | 8 |
| 13 | talc (*23) | 3.5 |
| 14 | mica (*23) | 4.5 |

(*2) the same as Table 3
(*23) a powder surface-treated with KF-9909 (triethoxysilylethylpolydimethylsiloxyethylhexyl dimethicone, available from Shin-Etsu Chemical Co., Ltd.)
(*24) decamethylcyclopentasiloxane solution of trimethylsiloxy silicate (available from Shin-Etsu Chemical Co., Ltd.)
(*25) a silicone composite powder having an average particle size of 2 μm (available from Shin-Etsu Chemical Co., Ltd.)

From the results of examples 1 to 19, it was revealed that the inventive gel paste composition contains a crosslinking organopolysiloxane having improved compatibility with ethylhexyl methoxycinnamate and water, and thus exhibits excellent dispersibility when blended to a cosmetic thereby providing good feeling and cosmetic sustainability.

It should be noted that the present invention is not limited to the above-described embodiments. The above-described embodiments are described for illustrative purposes, and those having substantially the same configuration and those providing the same operational advantage as the technical concept described in the claims of the present invention are all encompassed in the technical scope of the present invention.

The invention claimed is:

1. A gel paste composition comprising:
   (A) a crosslinking organopolysiloxane; and
   (B) a liquid oil,
   wherein the crosslinking organopolysiloxane (A) is obtained by reacting an organohydrogenpolysiloxane shown by the following general formula (I) with a polyoxyalkylene compound shown by the following general formula (II) and a polyoxyalkylene compound shown by the following general formula (III) in the presence of a catalyst for hydrosilylation reaction, the component (A) containing polyoxyethylene units in an amount in a range of 30 wt % to 60 wt % and at least one of absorbs and swells with each of water and ethylhexyl methoxycinnamate (OMC):

where each $R^1$ may be the same or different and represents a substituted or unsubstituted monovalent hydrocarbon group having 1 to 30 carbon atoms and not having an alkenyl group, and "a" and "b" each represent a positive number satisfying $1.0 \leq a \leq 2.5$, $0.001 \leq b \leq 1.2$, and $1.001 \leq a+b \leq 2.6$,

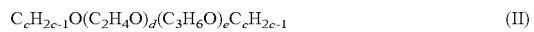

where "c" represents an integer of 2 to 6, and "d" and "e" each represent an integer satisfying $5 \leq d \leq 200$ and $0 \leq e \leq 200$,

where $R^2$ represents a hydrogen atom, a monovalent hydrocarbon group having 1 to 10 carbon atoms, or —(CO)$R^3$ where $R^3$ represents an alkyl group having 1 to 5 carbon atoms.

2. The gel paste composition according to claim 1, wherein the organohydrogenpolysiloxane used to obtain the crosslinking organopolysiloxane (A) is shown by the following general formula (V):

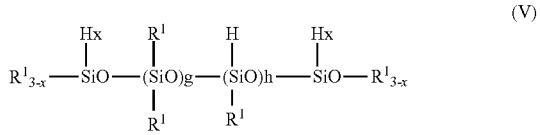

where "g" and "h" represent an integer satisfying $0 \leq g \leq 300$ and $0 \leq h \leq 300$; "x" is 0 to 2, and $h+x \geq 2$.

3. The gel paste composition according to claim 1, wherein the liquid oil (B) is selected from a silicone oil and an ester oil.

4. The gel paste composition according to claim 2, wherein the liquid oil (B) is selected from a silicone oil and an ester oil.

5. A cosmetic comprising a gel paste composition according to claim 1.

6. The cosmetic according to claim 5, further comprising an oil component (C) other than the liquid oil (B).

7. The cosmetic according to claim 5, wherein the cosmetic is an emulsified cosmetic and contains water and a water-soluble polymer in a continuous phase.

8. The cosmetic according to claim 7, wherein the water-soluble polymer is an alkali-thickened vinyl polymer or an acrylamidosulfonic acid polymer.

9. The cosmetic according to claim 7, wherein the emulsified cosmetic contains a surface-hydrophobized powder in an oil phase.

10. The cosmetic according to claim 9, wherein the surface-hydrophobized powder is a hydrophobized pigment.

* * * * *